(12) United States Patent
Pepper et al.

(10) Patent No.: US 11,464,556 B2
(45) Date of Patent: Oct. 11, 2022

(54) BONE FIXATION DEVICE AND METHOD

(71) Applicant: NEXTREMITY SOLUTIONS, INC., Warsaw, IN (US)

(72) Inventors: John R. Pepper, Cheshire, CT (US); Ryan D. Schlotterback, Fort Wayne, IN (US)

(73) Assignee: MEDARTIS AG, Basel (CH)

( * ) Notice: Subject to any disclaimer, the term of this patent is extended or adjusted under 35 U.S.C. 154(b) by 213 days.

(21) Appl. No.: 16/678,330

(22) Filed: Nov. 8, 2019

(65) Prior Publication Data

US 2020/0146735 A1 May 14, 2020

Related U.S. Application Data

(60) Provisional application No. 62/757,528, filed on Nov. 8, 2018.

(51) Int. Cl.
| | |
|---|---|
| *A61B 17/86* | (2006.01) |
| *A61B 17/84* | (2006.01) |
| *A61B 17/88* | (2006.01) |
| *A61B 17/56* | (2006.01) |
| *A61B 17/00* | (2006.01) |

(52) U.S. Cl.
CPC ........ *A61B 17/8685* (2013.01); *A61B 17/864* (2013.01); *A61B 17/8635* (2013.01); *A61B 17/846* (2013.01); *A61B 17/861* (2013.01); *A61B 17/8875* (2013.01); *A61B 2017/00004* (2013.01); *A61B 2017/568* (2013.01)

(58) Field of Classification Search
CPC ................... A61B 17/8685; A61B 2017/00004
See application file for complete search history.

(56) References Cited

U.S. PATENT DOCUMENTS

| | | | | |
|---|---|---|---|---|
| 6,916,321 | B2* | 7/2005 | TenHuisen | ......... A61B 17/8685 606/312 |
| 8,894,661 | B2 | 11/2014 | McDevitt et al. | |
| 9,138,219 | B2 | 9/2015 | Horrell et al. | |
| 2002/0198527 | A1 | 12/2002 | Muckter | |
| 2009/0198287 | A1 | 8/2009 | Chiu | |
| 2011/0054476 | A1* | 3/2011 | Nardini | ................ A61B 17/863 606/70 |

OTHER PUBLICATIONS

International Search Report and Written Opinion for International Patent Application No. PCT/US2019/060503 dated Jan. 16, 2020.

* cited by examiner

*Primary Examiner* — Olivia C Chang
(74) *Attorney, Agent, or Firm* — Heslin Rothenberg Farley & Mesiti P.C.; Victor A. Cardona, Esq.

(57) ABSTRACT

The present invention provides, in one aspect, a bone fixation device, the bone fixation device having a shaft, the shaft including a drive end and a tip end, at least a portion of the shaft configured to anchor into bone. The shaft further includes a first non-resorbable section extending from the tip end of the shaft, a second non-resorbable section extending from the drive end of the shaft, and a resorbable section. The resorbable section includes a tip side and a drive side, the resorbable section is between the first non-resorbable section and the second non-resorbable section, with the tip side of the resorbable section coupling to the first non-resorbable section and the drive side coupling to the second non-resorbable section.

8 Claims, 9 Drawing Sheets

BONE FIXATION DEVICE AND METHOD

CROSS-REFERENCE TO RELATED APPLICATIONS

This application claims priority under 35 U.S.C. § 119 to U.S. Provisional Application No. 62/757,528, filed Nov. 8, 2018, which is herein incorporated by reference in its entirety.

BACKGROUND OF THE INVENTION

Technical Field

The present invention generally relates to bone fixation devices. More particularly, the present invention relates to resorbable and partially resorbable bone fixation devices.

Background Information

A syndesmosis is a joint formed of approximately parallel bones joined to each other by fibrous connective tissue. An example of such a joint includes the interosseous ligament joining the tibia and the fibula. Syndesmotic injuries require reduced motion to heal. To limit motion, screws may be inserted to fasten the tibia and fibula to limit motion of the bones relative to each other. However, as the bones and surrounding tissue heal, motion returns to the joint and fixation screws often break, requiring hardware removal.

Thus, a need exists for bone fixation for a limited period and providing for movement thereafter, without having to perform hardware removal surgery.

SUMMARY OF THE INVENTION

A bone fixation device constructed in accordance with one or more aspects of the present invention may include a shaft. The shaft includes a drive end and a tip end. At least a portion of the shaft is configured to anchor into a bone. The shaft further includes a first non-resorbable section extending from the tip end of the shaft, a second non-resorbable section extending from the drive end of the shaft, and a resorbable section. The resorbable section includes a tip side and a drive side. The resorbable section is positioned between the first non-resorbable section and the second non-resorbable section. The tip side of the resorbable section couples to the first non-resorbable section and the drive side couples to the second non-resorbable section.

In another aspect, a bone fixation device is provided, the bone fixation device having a shaft, the shaft including a drive end and a tip end, and at least a portion of the shaft is configured to anchor into bone. The shaft further includes, a resorbable section and at least one non-resorbable section, the resorbable section coupling to the at least one non-resorbable section, with the resorbable section extending from the drive end of the shaft, and the non-resorbable section extending In another aspect, a method for temporarily immobilizing a tibia and a fibula that includes preparing the tibia and the fibula for inserting a bone fixation device is disclosed. The method further includes inserting a bone fixation device through the tibia and the fibula, the bone fixation device including a shaft, the shaft including a drive end and a tip end, at least a portion of the shaft configured to anchor into a bone. The shaft further includes a first non-resorbable section extending from the tip end of the shaft, a second non-resorbable section extending from the drive end of the shaft, and a resorbable section, with the resorbable section including a tip side coupled to the first non-resorbable section and a drive side coupled to the second non-resorbable section, and with the resorbable section being between the first non-resorbable section and the second non-resorbable section. The method further includes positioning the bone fixation device so that the resorbable section is between the fibula and the tibia and the portion of the shaft configured to anchor within a bone.

These, and other objects, features and advantages of this invention will become apparent from the following detailed description of the various aspects of the invention taken in conjunction with the accompanying drawings.

DETAILED DESCRIPTION OF THE INVENTION

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Thus, all the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

The following description references systems, methods, and apparatuses for use in bone fixation involving bones having a syndesmotic ligament. However, those possessing an ordinary level of skill in the relevant art will appreciate that fixation of other bones are suitable for use with the foregoing systems, methods, and apparatuses. Likewise, the various figures, steps, procedures, and work-flows are presented only as an example and in no way limit the systems, methods or apparatuses described to performing their respective tasks or outcomes in different time-frames or orders. The teachings of the present invention may be applied to any larger bone and smaller bone.

Furthermore, there is no intention to be bound by any expressed or implied theory presented in the preceding technical field, background, brief summary, or the following detailed description. It is also to be understood that the specific devices and processes illustrated in the attached drawings, and described in the following specification, are simply exemplary embodiments of the inventive concepts. Hence, specific dimensions and other physical characteristics relating to the embodiments disclosed herein are not to be considered as limiting, unless expressly stated otherwise.

The various embodiments described herein provide for systems, apparatuses, devices, and methods for bone fixation related to soft and fibrous connective tissue healing. The various figures and description may refer to the tibia, fibula, and the adjacent interosseous ligament or syndesmotic ligament. However, one having ordinary skill in the art will understand that that the following systems, apparatuses, devices, and methods for resorbable and partially resorbable bone fixation devices may be used with other joints having a syndesmosis, such as the acromioclavicular joint or other adjacent bones joined to each other by fibrous connective tissue.

In one aspect of the invention, a resorbable material may also be referred to as an absorbable material or a reabsorbable material. The various embodiments described provide for resorbable sections. Resorption involves the breakdown and assimilation of an object due to, for example, corrosion within a body as a result of exposure to fluids. Magnesium alloys such as, for example, magnesium oxide, are materials that lose substance or break down within the body. After breakdown, the resorptive material may be, for example, absorbed, reabsorbed, or expelled and would not need to be surgically removed. In another aspect of the invention, a resorbable bone fixation device may also be referred to as a bioabsorbable bone fixation device. In a further aspect of the invention, non-resorbable or non-resorptive sections or materials are those that may, for example, resist breakdown within the body.

Referring to the drawings, wherein like reference numerals are used to indicate like or analogous components throughout the several views, and with particular reference to FIGS. 1-17 a bone fixation device is depicted in various embodiments including inserted into bones of a leg. The bone fixation device depicted in FIGS. 1-12 may, for example, be entirely fabricated from a resorptive material or be sectioned into resorptive material and a non-resorptive material sections.

Figure 1:
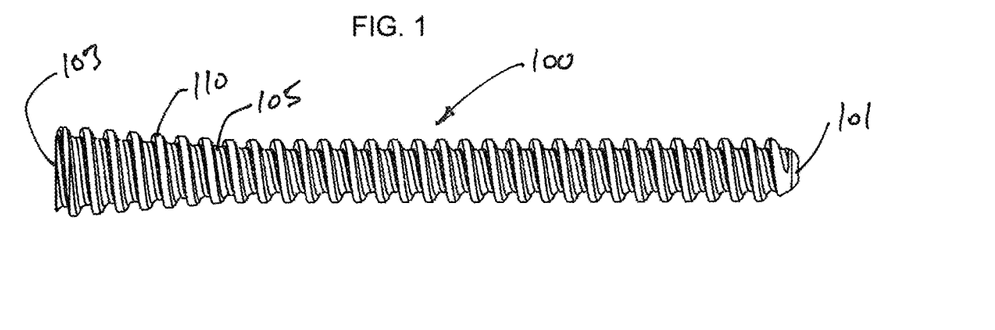
FIG. 1 is a perspective view of a resorbable bone fixation device, in accordance with an aspect of the present disclosure.

Referring to FIG. 1, an embodiment of a bone fixation device 100 is depicted having a shaft 105, a threading 110, a drive end 103, and a tip 101. Drive end 103 is opposite tip 101 with shaft 105 extending therebetween. Shaft 105 may be, for example, an elongated cylinder or a screw root. Threading 110 protrudes from shaft 105 and is depicted extending in a spiral from drive end 103 to approximately tip 101. Bone fixation device 100 is depicted as fully threaded with a constant pitch. Threading 110 may have a diameter range from, for example, approximately 3 mm to 7 mm, and more specifically have a diameter of approximately 4.5 mm. Shaft 105 may have a diameter with a range of, for example, approximately 2 mm to 6.5 mm, and more specifically have a diameter of approximately 3.5 mm. The pitch or the distance between subsequent peaks of threading may range from, for example, approximately 0.75 mm to 3 mm, and more specifically have an approximate pitch of 1.25 mm. Bone fixation device 100 may have, for example, a length from drive end 103 to tip 101 ranging from approximately 20 mm to 150 mm. Sizing selection may, for example, vary with what is surgically desired, including bone density, bone sizing, and bone and tissue damage.

Figure 2:
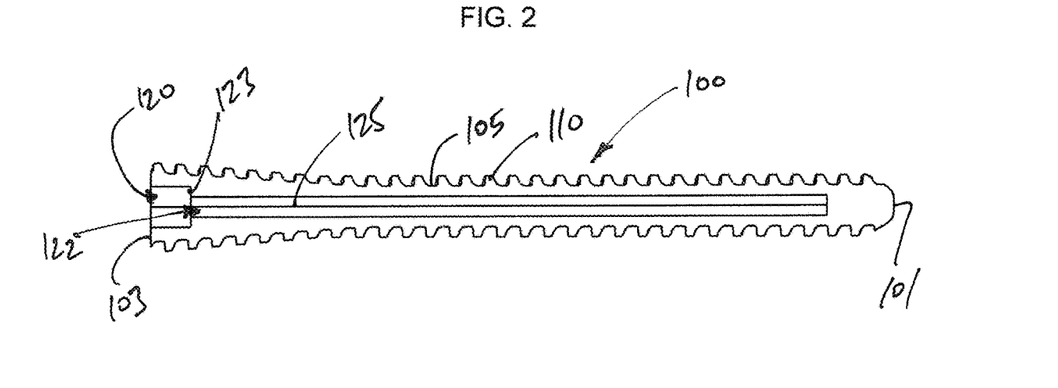
FIG. 2 is a longitudinal cross-section of the resorbable bone fixation device of FIG. 1, in accordance with an aspect of the present disclosure.

Referring to FIG. 2, shaft 105 may, for example, have a hollow interior with a drive slot 120 extending from drive end 103 into shaft 105 to a base end 123, in the direction of tip 101. Drive end 103 has a circumference and drive slot 120 is inset from the drive end circumference. Base end 123 is depicted with an opening 122 extending towards tip 101 within shaft 105 and forming a cannula 125. Drive slot 120 is configured (e.g. shaped and dimensioned) to accommodate a driver end of a driving device such as, for example, a screwdriver. Drive slot 120 is depicted as being hexagonal. Cannula 125 is also depicted as being hexagonal, however cannula 125 may be, for example, a multi-contoured shape or any shape that promotes torque transmission from drive end 103 through bone fixation device 100. Cannula 125 is depicted as having a narrower opening 122 than drive slot 120 at base 123. Base 123 provides a stop for a driver inserted into drive 120. Cannula 125 may be approximately 1 mm to 3 mm in diameter and may have a length from approximately 10 mm to the entire interior length of shaft 105, extending through tip 101. While bone fixation device 100 is depicted with a cannula 125, there may be other embodiments that are without a cannula.

With reference to FIGS. 1-2, bone fixation device 100 is depicted as a screw and may be, for example, fabricated from a resorptive material. The resorptive material may include, for example, magnesium alloys and more specifically, magnesium oxide. Bone fixation device 100 is depicted as a single resorbable component, with shaft 105 and threading 110 between and including tip 101 and drive end 103 being fabricated from a resorptive material.

Figure 3:
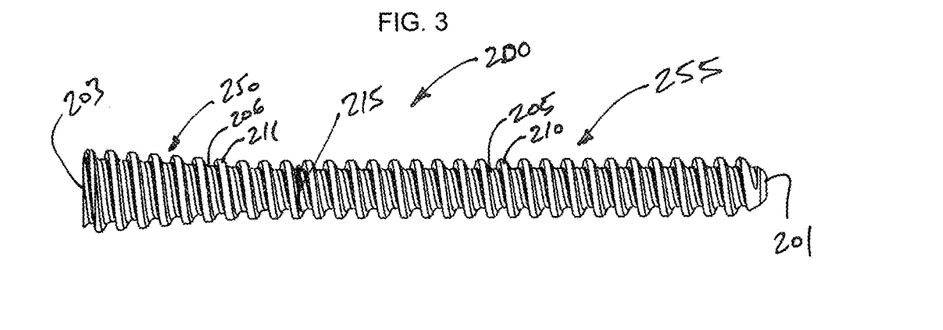
FIG. 3 is a perspective view of a two section partially resorbable bone fixation device, in accordance with an aspect of the present disclosure.

Referring to FIG. 3, a bone fixation device 200 is depicted as a screw having a resorbable section 250 and a non-resorbable section 255 between a drive end 203 opposite a tip 201. Resorbable section 250 extends from drive end 203 towards tip 201. Resorbable section 250 has a shaft 206 with threading 211 protruding outward, and threading 211 is depicted extending in a spiral from approximately drive end 203 towards tip 201. Non-resorbable section 255 extends from tip 201 towards drive end 203 and is depicted extending in a spiral from approximately tip 201 towards drive end 203. Non-resorbable section 255 has a shaft 205 with threading 210 protruding outwards. Resorbable section 250 and non-resorbable section 255 are configured (e.g. shaped and dimensioned) for connection at an interface 215. Shaft 205 and shaft 206 may have, for example, an approximately similar diameter and pitch. Threading 211 and threading 210 may have, for example, an approximately similar diameter. Bone fixation device 200 is depicted as fully threaded with a constant pitch, with resorbable section 250 and non-resorbable section 255 configured (e.g. shaped and dimensioned) to, for example, approximately match shaft 206 with shaft 205 and threading 211 with threading 210, forming a continuous body or screw root having continuous threading from drive end 203 to tip 201. Individual sections (e.g. resorbable section 250 and non-resorbable section 255) may vary in size but bone fixation device 200 has approximately the same sizing as screw 100, and for the sake of brevity, additional sizing details regarding screw diameter, threading, length, and pitch will not be repeated.

Figure 4:
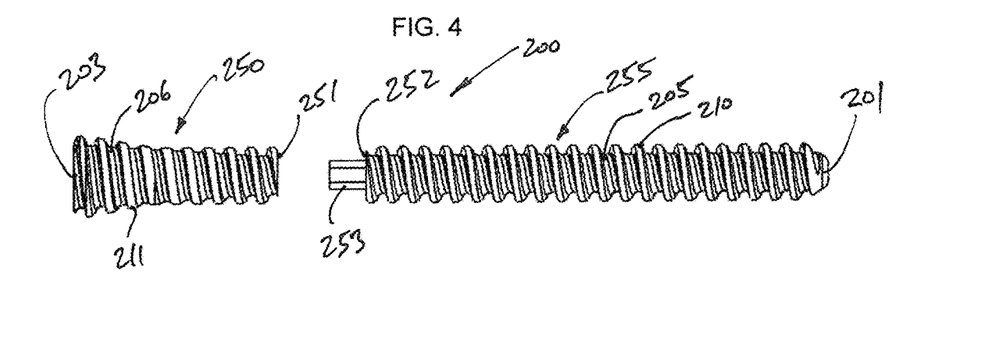
FIG. 4 is an exploded perspective view of the two section partially resorbable bone fixation device of FIG. 3, in accordance with an aspect of the present disclosure.

With reference to FIG. 4, resorbable section 250 has engagement face 251 opposite drive end 203 and non-resorbable section 255 has engagement face 252 opposite tip 201. Extending from face 252 is a protrusion 253, insertable into resorbable section 250.

Figure 5:
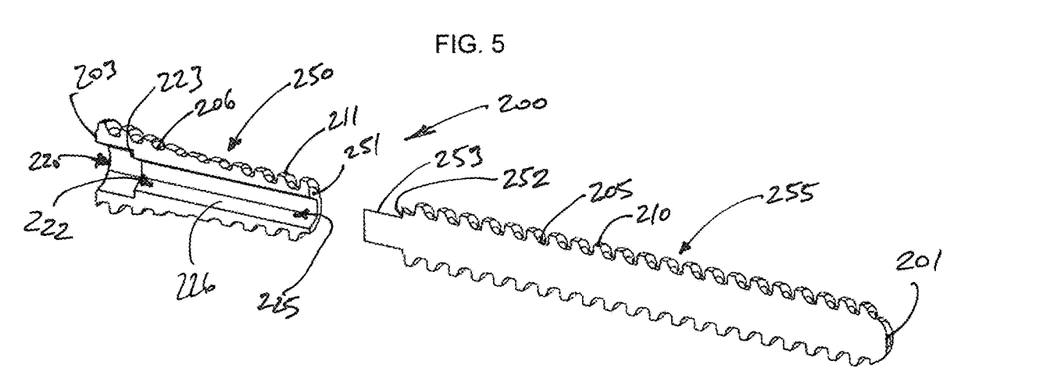
FIG. 5 is an exploded cross-section view of the two section partially resorbable bone fixation device of FIG. 3, in accordance with an aspect of the present disclosure.

With reference to FIG. 5, resorbable section 250 has a drive slot 220 extending from drive end 203 toward tip 201 into shaft 206 to drive base 223. Drive base 223 has an opening 222 extending into shaft 206 towards tip 201 to an opening 225 in face 251 and forming an engagement slot 226. Drive end 203 has a circumference and drive slot 220 is inset from the circumference. Drive slot 120 is configured (e.g. shaped and dimensioned) to accommodate a driver end of a driving device such as, for example, a screwdriver. Drive slot 220 is depicted as having a hexagonal shape.

With reference to FIGS. 3-5, protrusion 253 is configured (e.g. shaped and dimensioned) for insertion into engagement slot 226, such that engagement face 252 and engagement face 251 opposably contact forming interface 215. Resorbable section 250 and non-resorbable section 255 may, for example, be connected by protrusion 253 being press fit into engagement slot 226. Protrusion 253 and engagement slot 226 are both depicted as being hexagonal. Torque applied at drive 220 is transmitted from drive end 203 to tip 201 along bone fixation device 200. Protrusion 253 and engagement slot 226 may have, for example, a multi-contoured shape or any shape that promotes torque transmission between resorbable section 250 and non-resorbable section 255. Overlap as protrusion 253 is within engagement slot 226 and shape engagement between the shape of protrusion 253 and the shape of engagement slot 226 promote torque transmission.

With further reference to FIGS. 3-5, resorbable section 250 may be fabricated from, for example, magnesium oxide. Non-resorbable section 255 may be fabricated from a polymer such as, for example, polyether ether ketone or a metal such as, for example, titanium or stainless steel.

Figure 6:
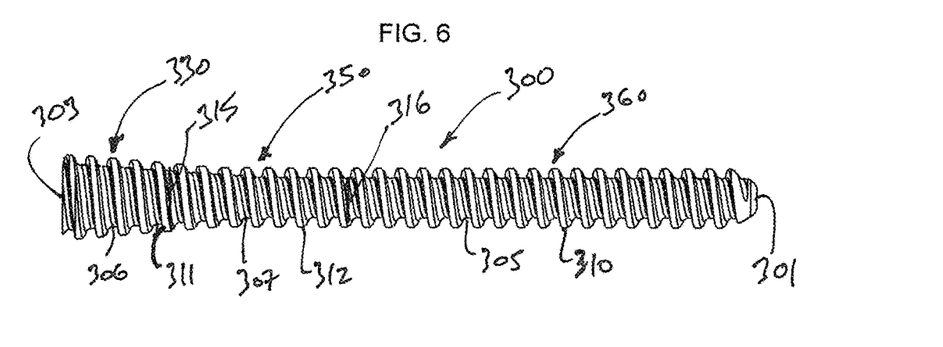
FIG. 6 is a perspective view of a three section partially resorbable bone fixation device, in accordance with an aspect of the present disclosure.

With reference to FIG. 6, a bone fixation device 300 is depicted as a screw having a first section 330, a second section 350, and a third section 360. First section 330 may, for example, extend from drive end 303 in the direction of tip 301 of bone fixation device 300. Third section 360 may extend, for example, from tip 301 towards drive end 303. Second section 250 may, for example, be positioned between first section 330 and third section 360 with first section and second section meeting at first interface 315 and third section and second section meeting at second interface 316. First section 330 has a shaft 306 with threading 311 extending outwards from shaft 306. Second section 350 has a shaft 307 with threading 312 extending outwards from shaft 307. Third section 360 has shaft 305 with threading 310 extending outwards from shaft 305.

Figure 7:
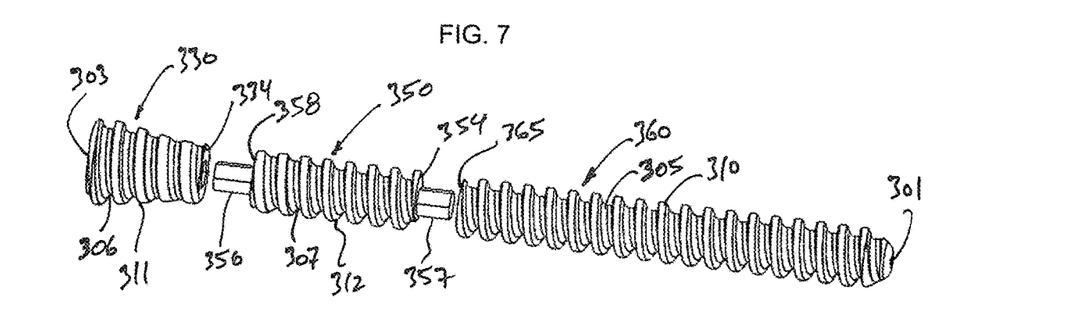
FIG. 7 is an exploded perspective view of the three section partially resorbable bone fixation device of FIG. 6, in accordance with an aspect of the present disclosure.

With reference to FIG. 7, first section 330 has a first section engagement face 334 opposite drive end 303. Second section has a first protrusion 356 extending from a first end 358 opposite a second protrusion 357 extending from a second end 254. First protrusion 356 is insertable into first section 330 with second section 350 engaging with first section 330 at first end 358. First section engagement face 334 and first end 358 are opposably in contact forming a first engagement interface 315. Second section 350 may, for example, extend from engagement interface 315 in the direction of tip 301 to second end 354. Second protrusion 357 is insertable into third section 360 with second section 350 engaging with third section 360 at a third section engagement face 365. Third section engagement face 365 and second end 354 are opposably in contact forming a second engagement interface 316. First section 330 and third section 360 are fabricated from a non-resorptive material such as, for example, polyether ether ketone, titanium, or stainless steel. Second section 350 is fabricated from a resorptive material such as, for example, magnesium alloy and more specifically magnesium oxide.

Figure 8:
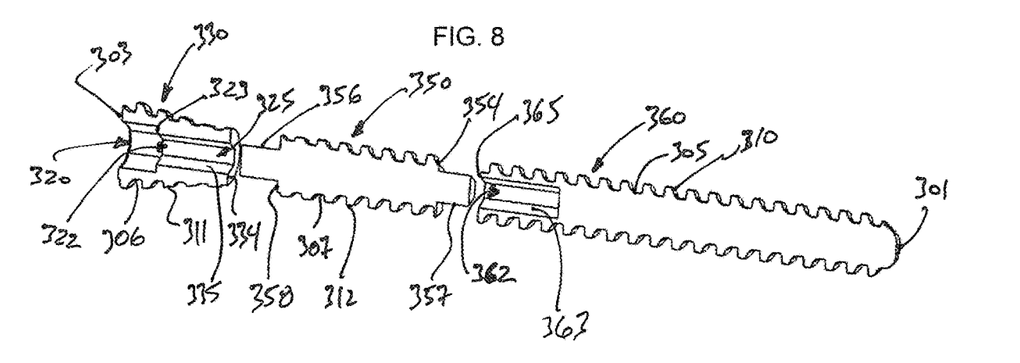
FIG. 8 is an exploded cross-section view of the three section partially resorbable bone fixation device of FIG. 6, in accordance with an aspect of the present disclosure.

With reference to FIG. 8, first section 330 has a drive slot 320 extending from drive end 303 into first section 330 towards first section engagement face 334 to drive base 323. Drive end 303 has a circumference and drive slot 320 is inset from the circumference. Drive slot 320 is configured (e.g. shaped and dimensioned) to accommodate a driver end of a driving device such as, for example, a screwdriver. Drive slot 320 may be, for example, hexagonal. First section 330 further has a first engagement slot 335 extending between an opening 322 in drive base 323 and an opening 325 in first section engagement face 334. First section engagement face 334 has a circumference and opening 225 is inset from the circumference of first section engagement face 334. Third section has a second engagement slot 363 extending from an opening 362 in third section engagement face 365 into third section 360 towards tip 301. Third section engagement face 365 has a circumference. Second engagement slot 363 has an opening inset from the circumference of third section engagement face 365.

With reference to FIGS. 6-8, first protrusion 356 is configured (e.g. shaped and dimensioned) for engagement with first engagement slot 335. First protrusion 356 and first engagement slot 335 may be, for example, hexagonal in shape. Second protrusion 357 is configured (e.g. shaped and dimensioned) for engagement with second engagement slot 363. Second protrusion 357 and second engagement slot 363 may be, for example, hexagonal in shape. Torque applied at drive 320 is transmitted from drive end 303 to tip 301 along bone fixation device 300. Overlap as first protrusion 356 is within first engagement slot 335 and the shape engagement between the shape of first protrusion 356 and the shape of first engagement slot 335 promotes torque transmission. Overlap as second protrusion 357 is within second engagement slot 363 and the shape engagement between the shape of second protrusion 357 and the shape of second engagement slot 363 promotes torque transmission. First protrusion 356 and first engagement slot 335 may have, for example, a multi-contoured shape or any shape that promotes torque transmission between first section 330 and second section 350. Second protrusion 357 and second engagement slot 363 may have, for example, a circular multi-contoured shape or any shape that promotes torque transmission between second section 350 and third section 360. Thus, torque transmission between first section 330 and third section 360 is promoted through the connection configuration of first protrusion 356 and first engagement slot 335 and the connection configuration of second protrusion 357 and second engagement slot 363.

With further reference to FIGS. 6-8, inserting first protrusion 356 into first engagement slot 335 places first end 358 adjacent first section engagement face 334 and connects first section 330 to second section 350. First protrusion 356 may be, for example, press fit into first engagement slot 335. Inserting second protrusion 357 into second engagement slot 363 places second end 354 adjacent third section engagement face 365 and connects second section 350 to third section 360. Second protrusion 357 may be, for example, press fit into second engagement slot 363. Connecting first section 330 to second section 350 to third section 360 forms bone fixation device 300. Bone fixation device 300 is depicted as formed from first section 330, second section 350, and third section 360 connected to approximately match pitch and threading (e.g. threading 311, threading 312, and threading 310) forming an approximately continuous thread and with shaft 306, shaft 307, and shaft 305 connected to form a single body. Individual sections (e.g. first section 330, second section 350, and third section 360) may vary in size and length but bone fixation device 300 has approximately the same sizing as bone fixation device 100, and for the sake of brevity, additional sizing details regarding bone fixation device diameter, threading, length, and pitch will not be repeated.

Figure 9:
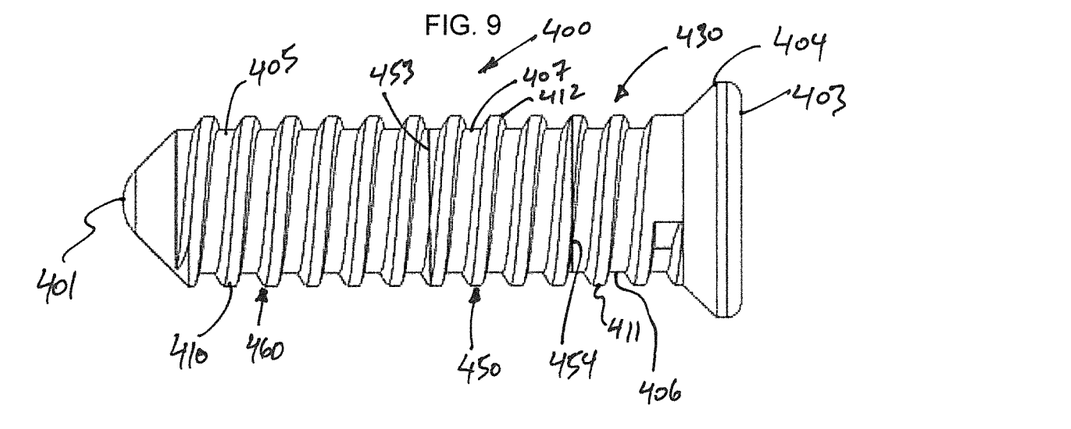
FIG. 9 is a side perspective view of another embodiment of a three section partially resorbable bone fixation device, in accordance with an aspect of the present disclosure.

With reference to FIG. 9 a bone fixation device 400 is depicted as a screw with a drive end 403 opposite a tip 401. Bone fixation device 400 further has a first section 430, a second section 450, and a third section 460. First section 430 extends from drive end 403 in the direction of tip 401 of bone fixation device 400 and third section 460, with second section 450 being between first section 430 and third section 460. First section 430 meets second section 450 at first interface 454 and third section 460 meets second section 450 at second interface 453. First section 430 has a shaft 406 with threading 411 extending outwards from shaft 406. Second section has a shaft 407 with threading 412 extending outwards from shaft 407. Third section 460 has a shaft 405 with threading 410 extending outwards from shaft 405. Drive end 403 is depicted as having a flared section extending circumferentially from shaft 405 towards drive end 403 and forming a conical head 404.

Figure 10:
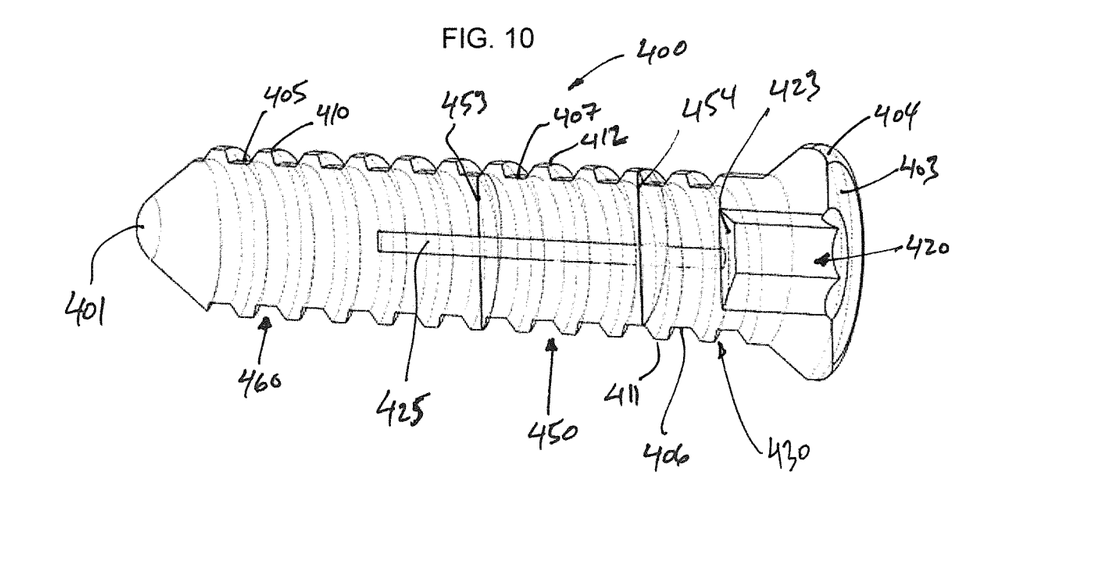
FIG. 10 is a cross-section view of the three section partially resorbable bone fixation device of FIG. 9, in accordance with an aspect of the present disclosure.

With reference to FIG. 10, drive end 403 is depicted as having a drive slot 420 inset from a circumference of drive end 403 and extending into first section 430, in the direction of tip 401 to a drive slot base 423. A cable 425 extends from drive slot base 423 in the direction of tip 401, through second section 450 and into third section 460. Cable 425 may be, for example, have a first end 423 fastened within first section 430 and a second end 426 fastened within third section 460. Cable 425 may have, for example, a length from approximately 5 mm to 25 mm. Cable 425 may have, for example, a diameter from approximately 1 mm to 2.5 mm. Cable 425 may, for example, be non-resorbable.

Figure 11:
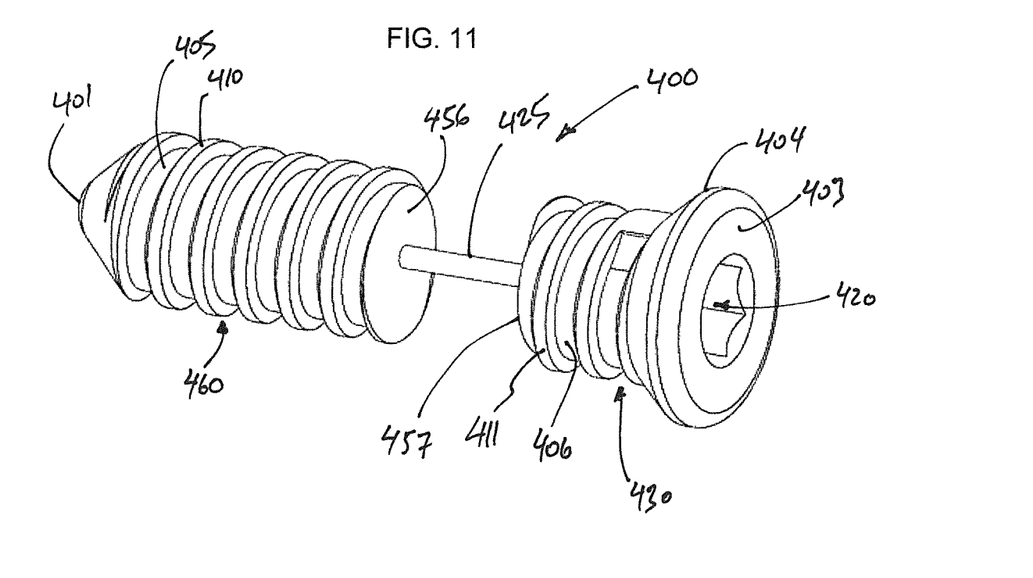
FIG. 11 is a rear perspective view of the three section partially resorbable bone fixation device of FIG. 9 post-resorption, in accordance with an aspect of the present disclosure.
Figure 12:
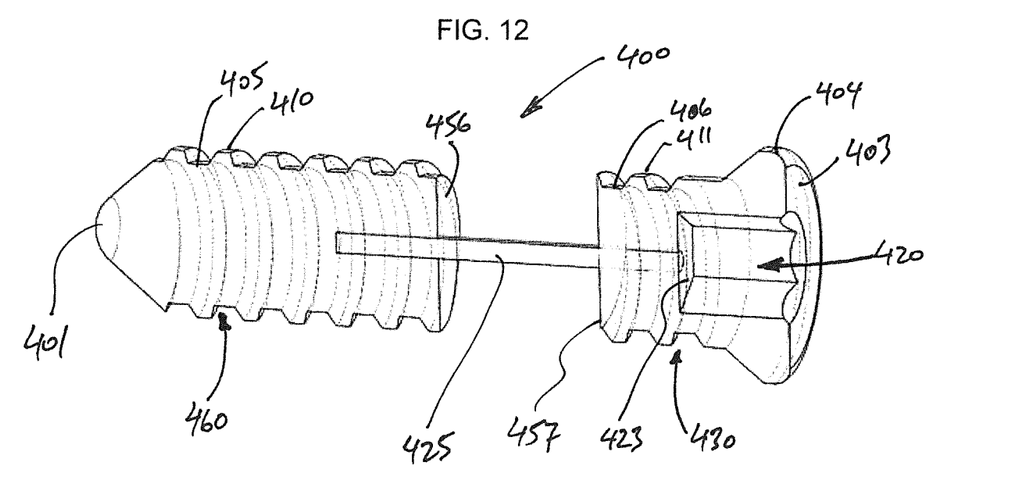
FIG. 12 is a cross section view the three section partially resorbable bone fixation device of FIG. 9 post-resorption, in accordance with an aspect of the present disclosure.

With reference to FIGS. 11 and 12, third section 360 extends from tip 401 in the direction of drive end 403 to a second engagement interface 453 with second section 450. First section 430 extends from drive end 403 in the direction of tip 401 engaging with second section 450 at a first engagement interface 454. First engagement interface 454 and second engagement interface 453 are at opposite ends of second section 450. First section 430 has a first face 457 opposite drive end 403 and third section 460 has a second face 456 opposite tip 401. Drive slot 420 is configured (e.g. shaped and dimensioned) to accommodate a driver end of a driving device such as, for example, a screwdriver. Drive slot 420 is depicted as having a hexagonal shape.

With reference to FIGS. 9-12, first section 430 and third section 460 are fabricated from a non-resorptive material such as, for example, polyether ether ketone, titanium, or stainless steel. Second section 450 is fabricated from a resorptive material such as, for example, a magnesium alloy and more specifically, magnesium oxide. Second section 450 may be, for example, molded into place between first face 457 and second face 456 around cable 425. Shaft 405, shaft 406, and shaft 407 are depicted as connected to form a single body. Threading 410, threading 411, and threading 412 are depicted as approximately matching and approximately continuous between drive head 404 and tip 401. Bone fixation device 400 may be, for example, fully threaded between tip 401 and head 404 with threading 410 approximately matching as first section 430 connects to second section 450 and second section 450 connects to third section 460. Individual sections (e.g. first section 430, second section 450, and third section 460) may vary in size but bone fixation device 400 has approximately the same sizing as bone fixation device 100, and for the sake of brevity, additional sizing details regarding bone fixation device diameter, threading, length, and pitch will not be repeated.

With further reference to FIGS. 11-14, cable 425 is depicted as extending from drive base 423 and into third section 460 and second section 450 may be, for example, molded around cable 425 and molded to and between first face 457 and second face 456. Torque applied at drive 420 is transmitted from drive end 403 to tip 401 along bone fixation device 400. Such construction provides torque transmission between first section 430, second section 450, and third section 460.

Figure 13:
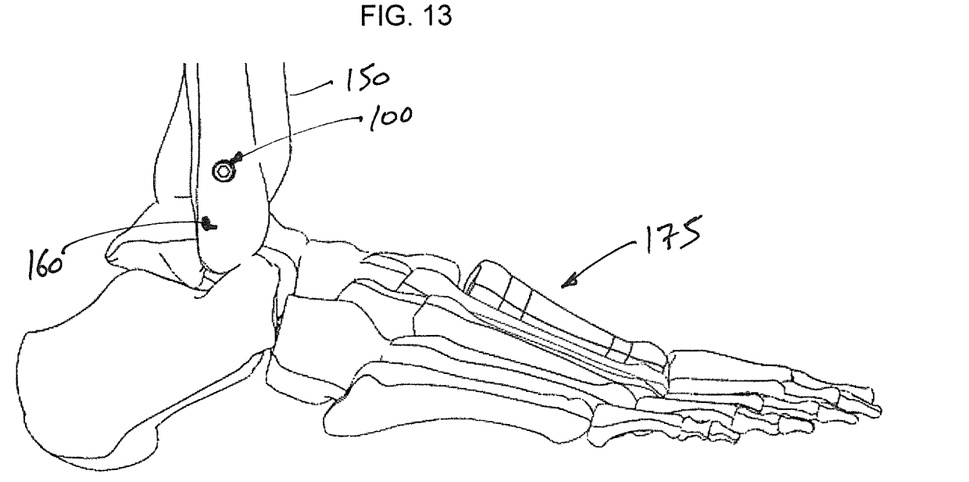
FIG. 13 is a side perspective view of a fibula and tibia connected with the resorbable bone fixation device of FIG. 1, in accordance with an aspect of the present disclosure.
Figure 14:
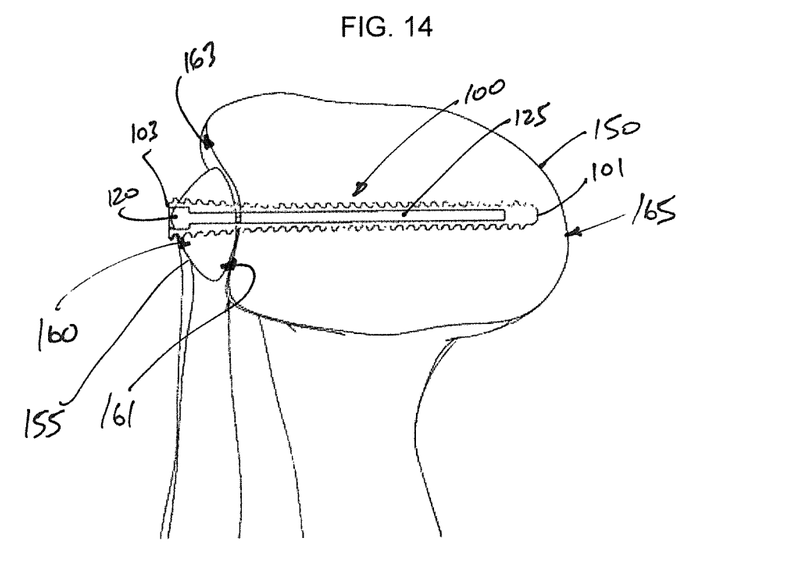
FIG. 14 is a transverse plane cross-section view of the resorbable bone fixation device of FIG. 1 connecting a fibula and a tibia, in accordance with an aspect of the present disclosure.
Figure 15:
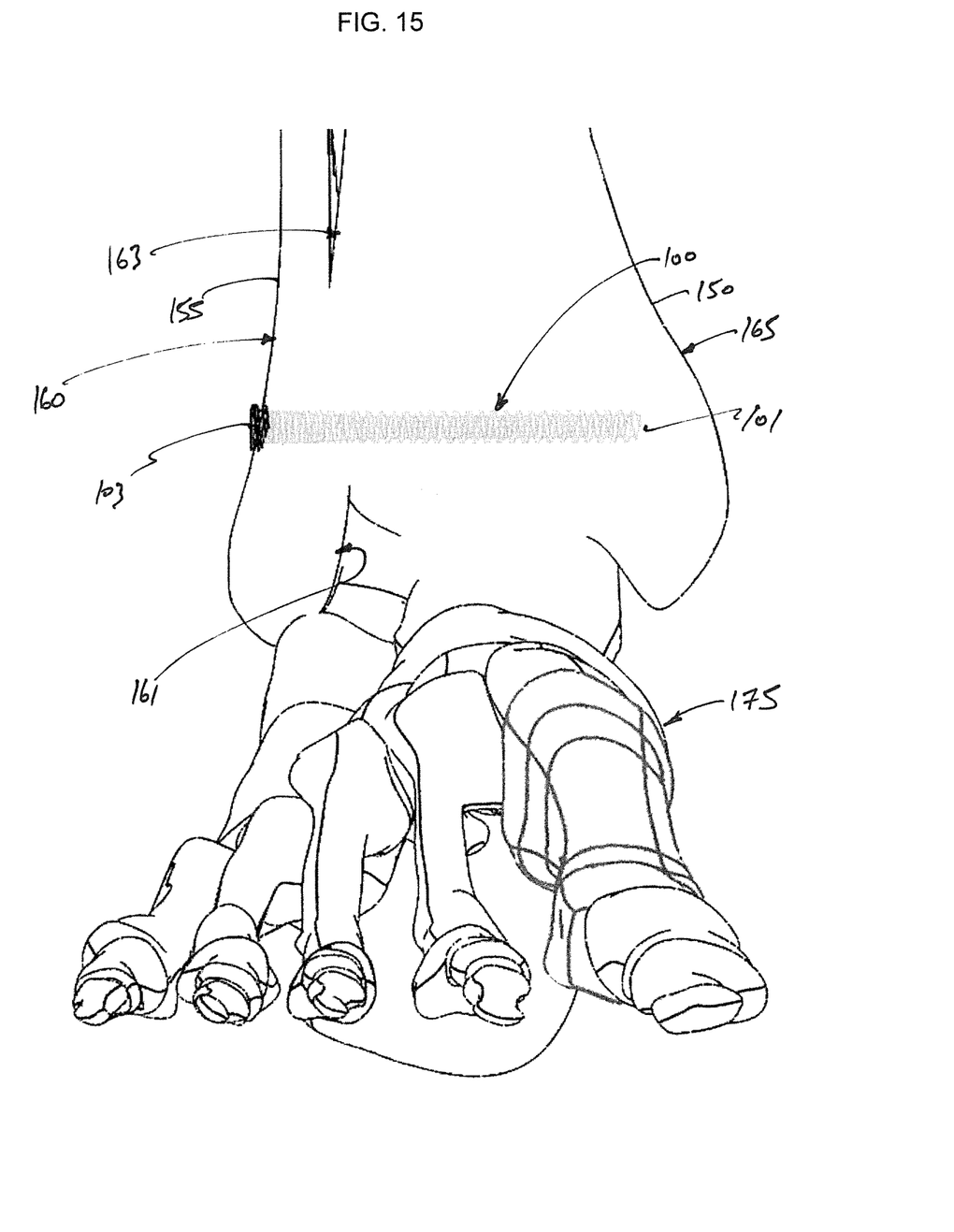
FIG. 15 is an anterior perspective cut-away view of the resorbable bone fixation device of FIG. 1 connecting a fibula and a tibia, in accordance with an aspect of the present disclosure.

Referring to FIGS. 13-15, bone fixation device 100 is depicted as inserted through a fibula 155 and into a tibia 150 above foot 175. Foot 175 is depicted as a right foot. Bone fixation device 100 is depicted as transversely positioned with tip end 101 passing through a lateral end 160 and a medial end 161 of fibula 155 and through a lateral end 163 of tibia 150 into tibia 150, with drive end 103 at approximately lateral end 160 of fibula 155 and tip 101 positioned towards a medial end 165 of tibia 150. Tip 101 may be, for example, inserted through medial end 165 of tibia 150 as surgically desired.

Figure 16:
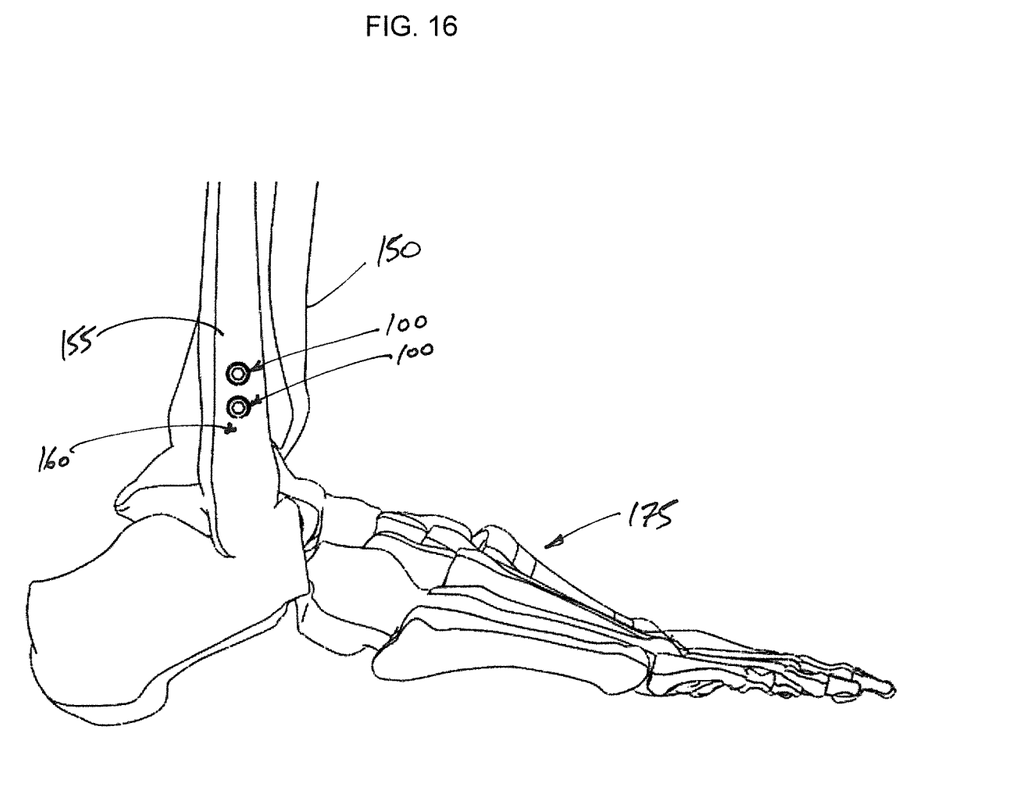
FIG. 16 is a side perspective view of a fibula and a tibia connected with a plurality of the resorbable bone fixation devices of FIG. 1, in accordance with an aspect of the present disclosure.

Referring to FIG. 16, tandem screws (i.e. two instances of bone fixation device 100), are depicted as inserted into fibula 155 and tibia 150, with an upper instance of bone fixation device 100 positioned above a lower instance of bone fixation device 100. Final positioning and the number of instances of bone fixation device 100 used may, for example, be determined based on bone condition (i.e. condition of fibula 155 and tibia 150), connective tissue damage, bone sizing, load conditions, and the extent of fixation desired.

Referring to FIGS. 1-2, bone fixation device 100 is fabricated from a resorptive material such as, for example, magnesium oxide. Cannula 125, as depicted in FIG. 2, may be plugged or partially plugged with a resorptive material such as, for example, magnesium oxide, to adjust and/or control the rate of resorption. Plugging or partially plugging cannula 125 may, for example, include using plugging material to cover a surface of cannula 125 or partially fill cannula 125 or obstructing opening 122. The volume and position of the plugging material may be, for example, configured (e.g. shaped, positioned, and dimensioned) to break bone fixation device 100 at an approximately desired position and/or within an approximately desired time period.

Further referring to FIGS. 13-16 a method of use includes drilling or tapping a joint bone (e.g. fibula 155 and tibia 150) and inserting bone fixation device 100 through fibula 155 and into tibia 150 to provide bone fixation. Threading 105 may, for example, provide anchoring for bone fixation device 100 into fibula 155 and tibia 150. The method further includes plugging or partially plugging cannula 125 to adjust the rate of resorption. Positioning plug material to adjust and/or control the break position of bone fixation device 100. Resorption of bone fixation device 100 is due to corrosion within a body due to exposure to body fluids. Threading 110, shaft 105, and exterior portions of bone fixation device 100 may be, for example, exposed to body fluids that encourage corrosion and material resorption. The presence of cannula 125 provides a place for body fluids such as, for example, blood to accumulate and resorb bone fixation device 100 from within. Using plugging material to plug, obstruct, or partially plug cannula 125 adjusts resorption time due to fluid interaction with those parts of bone fixation device 100 exposed to body fluids. This method may be repeated for inserting a second instance of bone fixation device 100 above or below the first instance of bone fixation device 100, or as is surgically desired.

With continued reference to FIGS. 13-16 bone fixation device 100 temporarily immobilizes adjacent bones, such as fibula 155 and tibia 150, relative to each other. By immobilizing the bones (e.g. fibula 155 and tibia 150), with respect to each other, the soft or fibrous tissue is provided an opportunity to heal. When bone fixation device 100 is resorbed or breaks because a sufficient portion of the resorptive material has been resorbed, bone movement may be restored. Due to resorption, bone fixation device 100 may, for example, not need to be removed. Resorption will continue and bone movement and healing continues as the bone fixation device is eventually fully resorbed.

Figure 17:
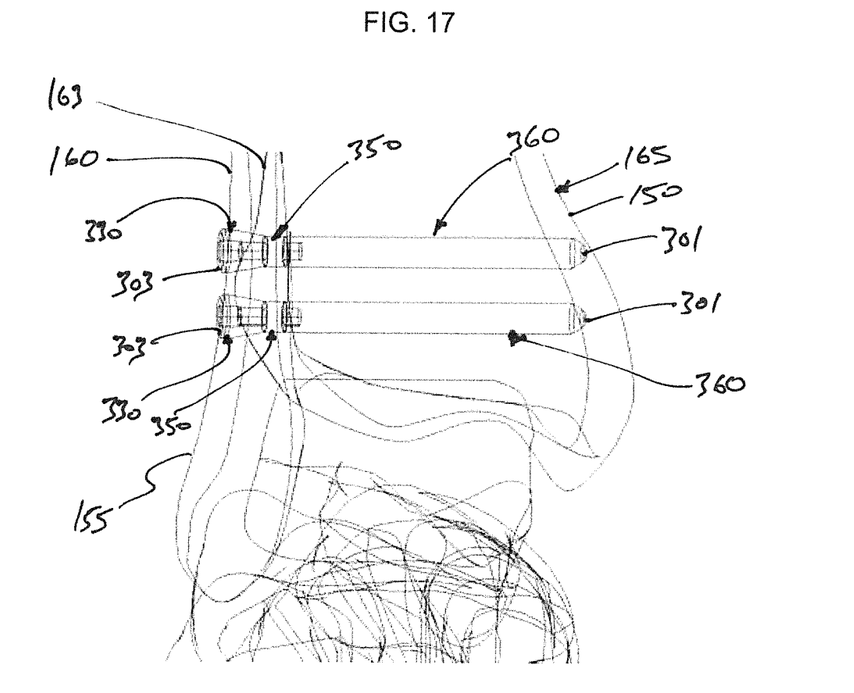
FIG. 17 is a front perspective cut-away view of the three section partially resorbable bone fixation device of FIG. 6 connecting a tibia and a fibula, in accordance with an aspect of the present disclosure.

With reference to FIG. 17 tandem screws (i.e. two instances of bone fixation device 300), are depicted as inserted through fibula 155 and into tibia 150 above foot 175. A first instance of bone fixation device 300 is depicted as transversely positioned with tip end 301 passing through lateral end 160 and medial end 161 of fibula 155 and through lateral end 163 of tibia 150 into tibia 150, with drive end 303 at approximately lateral end 165 of fibula 155 and tip 301 positioned towards medial end 165 of tibia 150. Threading 305, 306, and 307 may, for example, provide anchoring for bone fixation device 300 into fibula 155 and tibia 150. A second instance of bone fixation device 300 may be similarly inserted above or below the first instance as is surgically desired. Furthermore, tip 301 may be inserted through medial end 165 of tibia 150 as is surgically desired for one or both of the tandem screws (i.e. two instances of bone fixation device 300).

With further reference to FIGS. 6-8 and 13-17, bone fixation device 300 may be, for example, placed into fibula 155 and tibia 150 such that second section 350 is resorbed, leaving first section 330 within fibula 155 and third section 360 within tibia 150. Resorption of second section 350 includes resorption of protrusions (e.g. first protrusion 356 and second protrusion 357). Removal may not be necessary as first section may be completely within fibula 155 and third section completely within tibia 150. A space the size of resorbed second section 350 is created, with no contact between first section 330 and third section 360, and eliminates a need for removal. However, if removal of first section 330 is desired, first section 330 has a drive end 303 with drive slot 320 into which a screwdriver or other driving device (not shown) configured (e.g. shaped and dimensioned) for engagement with drive slot 320 may be inserted to remove first section. First section also has first engagement slot 335, and a screwdriver or other driving device (not shown) configured (e.g. shaped and dimensioned) for engagement into first engagement slot 335 may be inserted as a second means of removing first section 330. If removal of third section 360 is necessary or desired, a screwdriver or other driving device (not shown) configured (e.g. shaped and dimensioned) for insertion into second engagement slot 363 may be inserted and used to remove third section 360.

Continuing to refer to FIGS. 6-8 and 13-17, a method of use includes drilling or tapping a joint (e.g. fibula 155 and tibia 150), inserting bone fixation device 300 through fibula 155 and into tibia 150 providing bone fixation. Resorption of second section 350 is due to corrosion within a body due to exposure to fluids. Embodiments of bone fixation device 300 may include unthreaded regions, including second section 350 being unthreaded. Breaking second section 350 due to bone movement as tissue heals and resorption provide for fixation for a limited period with restored movement as healing and resorption progresses.

With reference to FIGS. 9-17, bone fixation device 400 may be inserted in a single or tandem configuration (e.g. two instances of bone fixation device 400) through fibula 155 and into tibia 150. Bone fixation device 400 may be, for example, inserted transversely with tip end 401 passing through lateral end 160 and medial end 161 of fibula 155 and through lateral end 163 of tibia 150 into tibia 150. Threading 405, 406, and 407 may, for example, provide anchoring for bone fixation device 400 into fibula 155 and tibia 150. Drive end 403 may be, for example, at or approximately flush with lateral end 165 of fibula 155 and tip 401 positioned towards medial end 165 of tibia 150. A second instance of bone fixation device 400 may be similarly inserted above or below the first instance as is surgically desired. Furthermore, tip 401 may be inserted through medial end 165 of tibia 150 as is surgically desired for one or both of the tandem screws (i.e. two instances of bone fixation device 400).

With further reference to FIGS. 9-17, bone fixation device 400 may be, for example, placed into fibula 155 and tibia 150 such that second section 450 is resorbed, leaving first section 430 within fibula 155 and connected to third section 460 within tibia 150 by cable 425. First section 430 and third section 460 may, for example, remain within the body as first section remains within fibula 155 and third section remains within tibia 150. Cable 425 may, for example, be flexible to provide for joint motion or motion of fibula 155 relative to tibia 150.

With reference to FIGS. 1-17, bone fixation devices 100, 200, 300, and 400 are described as being inserted laterally into fibula 155 and tibia 150. However, bone fixation devices 100, 200, 300, and 400 may include, for example, additional anterior/posterior positioning and/or angling and/or additional dorsal/plantar positioning and/or angling to achieve surgically desired insertion positioning.

With reference to FIGS. 3-5 and 13-17, bone fixation device 200 may be, for example, inserted through fibula 155 and into tibia 150. Bone fixation device 200 may be, for example, transversely positioned with tip end 201 passing through lateral end 160 and medial end 161 of fibula 155 and through lateral end 163 of tibia 150 into tibia 150, with drive end 203 at approximately lateral end 160 of fibula 155 and tip 201 positioned towards medial end 165 of tibia 150. Threading 205 and 206 may, for example, provide anchoring for bone fixation device 200 into fibula 155 and tibia 150. In other embodiments, tip 201 may be inserted through medial end 165 of tibia 150. Bone fixation device 200 may be inserted such that, for example, resorbable section extend into lateral end 163 of tibia 150. As resorbable section 250 breaks and/or is resorbed, non-resorbable section 255 may, for example, remain within tibia 150.

With reference to FIGS. 3-17 bone fixation devices 200, 300, and 400 temporarily immobilizes adjacent bones, such as fibula 155 and tibia 150, relative to each other. By immobilizing the bones (e.g. fibula 155 and tibia 150), with respect to each other, the soft or fibrous tissue is provided an opportunity to heal. When the resorbable sections of bone fixation devices 200, 300, and 400 are resorbed or break because a sufficient portion of the resorptive material has been resorbed, bone movement is no longer inhibited because the resorbable section has been resorbed. Due to resorption, bone fixation device 200, 300, and 400 do not need to be removed. However, non-resorbable sections (e.g. non-resorbable section 255, first section 330, third section 360) may be removed if desired and provide for drives (e.g. drive 220, drive 320, engagement slot 226, first engagement slot 335, and second engagement slot 363) that are removable using a driving device such as, for example, a screwdriver. Resorption will continue and bone movement and healing continues as the bone fixation device is eventually fully resorbed.

With reference to FIGS. 3-5, bone fixation device 200 is depicted as having engagement slot 226 extending from drive base 223 to engagement face 251. Engagement slot 226 may, for example, act as a cannula which may be plugged with a resorptive plug material to adjust the rate of resorption.

With Reference to FIGS. 1-12, bone fixation devices 100, 200, 300 and 400 are described as being fully threaded with a constant pitch. However, other embodiments may have a Herbert style screw with variable pitch, or a screw s with smooth shank section without full threading, or an ASTM profile screw form, or an ISO profile screw form. Bone fixation devices constructed in accordance with one or more aspects of the present invention may have embodiments that are, for example, self-tapping or non-self-tapping. Bone fixation devices 100, 200, and 300 are depicted as being headless however, other embodiments may, for example, have a head (e.g. head 404) as with bone fixation device 400. Furthermore, bone fixation device 400 is depicted with a head 404 but other embodiments may be, for example, headless.

With further reference to FIGS. 1-12, other embodiments may include anchoring means other than threading such as, for example, barbs, prongs, spikes, spurs, and protrusions extending outwards from shafts 105, 205, 206, 305, 306, 307, 405, 406, and/or 407.

With reference to FIGS. 3-5, resorbable section 250 extends from drive end 203 towards tip 201 and non-resorbable section 255 extends from tip 201 towards drive end 203. However, in alternative embodiments, resorbable section 250 and non-resorbable section 255 may be, for example, reversed with resorbable section 250 extending from tip end 201 towards drive end 203 and non-resorbable section 255 extending from drive end 203 towards tip end 201.

In alternative embodiments, the resorbable and non-resorbable sections may be interchanged. For example, first section 330 and third section 360 may be resorbable and second section 350 may be non-resorbable. In other embodiments, first section 330, second section 350, and third section 360 may be, for example, non-resorbable or resorbable as is surgically desired. In other examples, first section 430 and third section 460 as illustrated in FIGS. 9-12, may be, for example, resorbable and second section 450 may be, for example, non-resorbable. In certain other embodiments, first section 430, second section 450, and third section 460 may be, for example, non-resorbable or resorbable as is surgically desired. In addition, in still certain other embodiments, cable 325 may be, for example, resorbable or non-resorbable as is surgically desired.

In other embodiments, a plurality of resorbable sections and a plurality of non-resorbable sections may be provided with differing lengths, diameters, threading, and thread pitch to allow for size adjustment as surgically desired and to account for patient bone sizing and differing surgical circumstances.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

What is claimed is:

1. A bone fixation device, said bone fixation device comprising:
   a shaft, said shaft including a drive end and a tip end, at least a portion of said shaft configured to anchor into a bone, said shaft including:
      a first non-resorbable section extending from the tip end of said shaft;
      a second non-resorbable section extending from the drive end of said shaft;
      a resorbable section, said resorbable section including a tip side and a drive side, said resorbable section being positioned between the first non-resorbable section and the second non-resorbable section, the tip side of said resorbable section being coupled to the first non-resorbable section and the drive side being coupled to the second non-resorbable section;
   the first non-resorbable section having a slot for receiving a protrusion of the resorbable section, the slot extending from a first drive side of the first non-resorbable section toward the tip and the slot unconnected to the tip;

the first non-resorbable section, the resorbable section and the second non-resorbable section having an approximately continuous thread with an approximately matched pitch.

2. The bone fixation device of claim 1, wherein the resorbable section further includes a first protrusion, extending from the tip side, engaging with a first mating slot extending into the first non-resorbable section and a second protrusion, extending from the drive side, engaging with a second mating slot extending into the second non-resorbable section.

3. The bone fixation device of claim 2, wherein the first protrusion is a multi-contoured shape insertable into the first mating slot having a matching multi-contoured shape, and the second protrusion is a multi-contoured shape insertable into the second mating slot having a matching multi-contoured shape.

4. The bone fixation device of claim 3, wherein the first protrusion is press-fit into the first mating slot and the second protrusion is press fit into the second mating slot.

5. The bone fixation device of claim 3, wherein the first protrusion inserted into the first mating slot and the second protrusion inserted into the second mating slot promotes torque transmission along the shaft between the drive end and the tip end.

6. The bone fixation device of claim 1, wherein the drive end includes a drive end opening extending into the shaft.

7. The bone fixation device of claim 1, wherein at least a portion of the shaft is threaded.

8. The bone fixation device of claim 7, wherein at least a portion of the resorbable section is threaded.

* * * * *